(12) United States Patent
Guerin et al.

(10) Patent No.: US 11,986,815 B2
(45) Date of Patent: May 21, 2024

(54) PROCESSES AND SYSTEMS FOR PRODUCING AND/OR PURIFYING GALLIUM-68

(71) Applicant: SOCIETE DE COMMERCIALISATION DES PRODUITS DE LA RECHERCHE APPLIQUÉE SOCPRA SCIENCES ET GÉNIE S.E.C., Sherbrooke (CA)

(72) Inventors: Brigitte Guerin, Westbury (CA); Sebastien Tremblay, Sherbrooke (CA); Samia Ait-Mohand, Sherbrooke (CA); Aiman H. Alnahwi, Dammam (SA)

(73) Assignee: SOCIETE DE COMMERCIALISATION DES PRODUITS DE LA RECHERCHE APPLIQUÉE SOCPRA SCIENCES SANTE ET HUMAINES S.E.C., Sherbrooke (CA)

( * ) Notice: Subject to any disclaimer, the term of this patent is extended or adjusted under 35 U.S.C. 154(b) by 487 days.

(21) Appl. No.: 17/413,146

(22) PCT Filed: Dec. 10, 2019

(86) PCT No.: PCT/CA2019/051777
§ 371 (c)(1),
(2) Date: Jun. 11, 2021

(87) PCT Pub. No.: WO2020/118426
PCT Pub. Date: Jun. 18, 2020

(65) Prior Publication Data
US 2022/0044835 A1    Feb. 10, 2022

Related U.S. Application Data

(60) Provisional application No. 62/777,994, filed on Dec. 11, 2018.

(51) Int. Cl.
*B01J 47/026* (2017.01)
*A61B 6/03* (2006.01)
(Continued)

(52) U.S. Cl.
CPC .......... *B01J 47/026* (2013.01); *A61K 51/083* (2013.01); *B01J 39/26* (2013.01); *A61B 6/037* (2013.01);
(Continued)

(58) Field of Classification Search
CPC . B01J 47/026; B01J 39/26; B01J 39/05; B01J 45/00; B01J 49/60; A61K 51/083;
(Continued)

(56) References Cited

U.S. PATENT DOCUMENTS 10,522,261 B2 * 12/2019 DeGrado ............. B01J 20/3092
11,197,938 B1 * 12/2021 O'Hara ................. A61K 51/10

FOREIGN PATENT DOCUMENTS

CN         1454706       11/2003
JP       2012-078353      4/2012
(Continued)

OTHER PUBLICATIONS

International Search Report of PCT/CA2019/051777.
(Continued)

*Primary Examiner* — Krishnan S Menon
(74) *Attorney, Agent, or Firm* — NORTON ROSE FULBRIGHT CANADA LLP (57) ABSTRACT

The present disclosure relates processes and systems for producing and/or purifying $^{68}$Ga from an irradiated substrate of $^{68}$Zn. In some embodiments, the process rely on the use two cation-exchange chromatography columns to separate $^{68}$Ga from $^{68}$Zn and other radionuclides and metallic impurities. The process achieves a high overall yield of $^{68}$Ga and a high effective molar activity while being implementable in (Continued)

a time compatible with the short half-life of $^{68}$Ga. In additional embodiments, the process is implemented by an automated system.

11 Claims, 6 Drawing Sheets

(51) Int. Cl.
| | |
|---|---|
| *A61K 51/08* | (2006.01) |
| *B01J 39/26* | (2006.01) |
| *G21G 1/00* | (2006.01) |
| *G21G 1/10* | (2006.01) |

(52) U.S. Cl.
CPC ....... *G21G 2001/0021* (2013.01); *G21G 1/10* (2013.01)

(58) Field of Classification Search
CPC ........ A61K 51/088; A61B 6/037; G21G 1/10; G21G 2001/0021; G21G 1/001; H05H 6/00

See application file for complete search history.

(56) References Cited

FOREIGN PATENT DOCUMENTS

| | | |
|---|---|---|
| JP | 2017-003577 | 1/2017 |
| JP | 2017-521645 | 8/2017 |
| JP | 2018-002606 | 1/2018 |
| JP | 2018-190711 | 11/2018 |
| WO | 2018/039662 A1 | 3/2018 |

OTHER PUBLICATIONS

Lin et al. "Production of curie quantities of 68Ga with a medical cyclotron via the 68Zn(p,n)68Ga reaction" Appl. Rad. Iso. Dec. 9, 2017 (Dec. 9, 2017) 133, pp. 1-3.
Pandey et al. "Cyclotron production of68Ga via the 68Zn(p,n)68Ga reaction in aqueous solution" Am. J. Nucl. Med. Mol. Imaging 2014, 4(4), pp. 303-310.
Pandey et al. "Automated processing of cyclotron produced 68Ga using hydroxamate resin" J. Nucl. Med. May 1, 2017 (May 1, 2017) 58, Suppl 1, p. 333.
Dumulon-Perreault, V. et al. «Validation of 68Ga-4HMSA-PSMA, anovel PSMA radioligand for PET imaging of prostate cancer» J. Nucl. Med. May 1, 2019 (May 1, 2019), 60, Suppl. 1, p. 1044.
Pandey et al. "Cyclotron production of 68Ga in a liquid target: effects of solution composition and irradiation parameters" Nucl. Med. Biol. Mar. 2019, 74-75, pp. 49-55.
Alves, F., Alves, V.H., Neves, A.C.B., Do Carmo, S.J.C., Nactergal, B., Hellas, V., Kral, E., Gonçalves-Gameiro, C., Abrunhosa, A.J., 2017. Cyclotron production of Ga-68 for human use from liquid targets: From theory to practice. AIP Conf. Proc. 1845.
Blaser, J.P., Boehm, F., Marmier, P., Peaslee, D.C., 1950. Fonctions d'excitation de la réaction (p,n). (I). Helv. Phys. Acta 24, 3-38.
Hermanne, A., 1997. Evaluated cross section and thick target yield data of Zn+P processes for practical applications Private communication. Exfor: D4093 49.
Howe, H.A., 1958. (p,n) Cross Sections of Copper and Zinc. Phys. Rev. 109, 6-8.
Mueller, D., Klette, I., Baum, R.P., Gottschaldt, M., Schultz, M.K., Breeman, W.A.P., 2012. Simplified NaCl based68Ga concentration and labeling procedure for rapid synthesis of68Ga radiopharmaceuticals in high radiochemical purity. Bioconjug. Chem. 23, 1712-1717.
Nortier, F.M., Stevenson, N.R., Gelbart, W.Z., 1995. Investigation of the thermal performance of solid targets for radioisotope production. Nucl. Instruments Methods Phys. Res. Sect. A Accel. Spectrometers, Detect. Assoc. Equip. 355, 236-241.
Szelecsenyi, F., Boothe, T. e., Takâcs, S., Târkânyi, F., Tavano, E., 1998. Evaluated Cross Section and Thick Target Yield Data Bases of Zn + p Processes for Practical Applications. Appl. Radiat. Isot. 49, 1005-1032.
Velikyan, I., 2015. 68Ga-based radiopharmaceuticals: Production and application relationship, Molecules.
Verel, I., Visser, G.W.M., Boellaard, R., Marijke, ;, Walsum, S.-V., Snow, G.B., Van Dongen, G.A.M.S., 2003. 89 Zr Immuno-PET: Comprehensive Procedures for the Production of 89 Zr-Labeled Monoclonal Antibodies. J Nucl Med 44, 1271-1281.
English Translated Abstract of JP2017-521645.
English Translated Abstract of JP2017-003577.
English Translated Abstract of JP2018-190711.
English Translated Abstract of JP2012-078353.
English Translated Abstract of JP2018-002606.
English Translated Abstract of CN1454706.

\* cited by examiner

PROCESSES AND SYSTEMS FOR PRODUCING AND/OR PURIFYING GALLIUM-68

CROSS-REFERENCE TO RELATED APPLICATION

The present application claims priority from U.S. provisional patent application 62/777,994 filed on Dec. 11, 2018 and herewith incorporated in its entirety.

TECHNOLOGICAL FIELD

The present disclosure generally relates to the production and/or purification of gallium-68 ($^{68}$Ga) from an irradiated substrate of zinc-68 ($^{68}$Zn), and specifically to methods and system for producing and/or purifying $^{68}$Ga.

BACKGROUND $^{68}$Ga attracted increasing interest in recent years due to the expanding clinical applications of $^{68}$Ga-based radiopharmaceuticals. $^{68}$Ga is a positron emitting radioactive isotope with a short half-life ($t_{1/2}$=68 min). Because of this short half-life, it is critical that $^{68}$Ga be produced with high yield and high purity to minimize or entirely alleviate the need for extensive and time-consuming purification steps.

$^{68}$Ga is generally produced with $^{68}$Ge/$^{68}$Ga generators (Velikyan 2015). The productions methods are limited by the amount of loaded $^{68}$Ge activity (up to 1.85 GBq). Also, because of the longer half-life of $^{68}$Ge ($t_{1/2}$=271 days) compared to that of $^{68}$Ga, $^{68}$Ge has undesirable side effects in the human body and should be completely separated from $^{68}$Ga prior use. Known methods of separation of $^{68}$Ge from $^{68}$Ga generally do not provide a complete separation or a sufficient yield of $^{68}$Ga production and generator-based approaches deliver limited activity per elution (25-100 mCi) with restrictive waiting times between elutions (Alves et al., 2017; Velikyan 2015).

Alternatives to $^{68}$Ge/$^{68}$Ga generators for the production of $^{68}$Ga include cyclotrons. In cyclotron-based methods, a liquid or solid target of $^{68}$Zn is irradiated with a proton beam to produce $^{68}$Zn, $^{68}$Ga as well other radionuclide and metal contaminants. The subsequent purification steps are complex and compromised by the contamination with metallic ions (such as $Fe^{3+}$, $Cu^{2+}$, $Zn^{2+}$) such that cyclotron-based methods do not currently constitute a viable alternative to generator-based methods given the limited quantity and purity of $^{68}$Ga produced and the length of the purification process (Blaser et al., 1950; Hermanne, 1997; Howe, 1958; Szelecsenyi et al., 1998).

While the use of a liquid target benefits from a lower radiation exposure during handling, purification and labelling, it also offers limited activities of $^{68}$Ga and low production yield (Alves et al., 2017; Pandey et al., 2014). Conversely, the use of a solid target confers high production yields but suffers from long preparation, dissolution and purification times (Nortier et al., 1995; Alves et al., 2017; Lin et al., 2018).

With the increased demand of $^{68}$Ga in nuclear medicine for positron electron tomography (PET) imaging, there remains a need for cyclotron-based processes and systems that address the shortcomings above and enable the production of $^{68}$Ga with high yield, high purity (that is, free or substantially free of contaminants) and/or high effective molar activity (EMA) in large amounts and in a time compatible with the short half-life of $^{68}$Ga.

SUMMARY

The present disclosure concerns a process for purifying $^{68}$Ga produced by cyclotron.

According to a first aspect, the present disclosure provides a process for purifying $^{68}$Ga produced by cyclotron, the process comprising the steps of: (a) providing a solution comprising a mixture of $^{68}$Zn and $^{68}$Ga; (b) contacting the solution with a first chelating cation exchange column, the first chelating cation exchange column comprising a hydroxamate resin; (c) washing the first chelating cation exchange column obtained after step (b) to obtain a washed first chelating cation exchange column; (d) eluting the $^{68}$Ga from the washed first chelating cation exchange column to obtain a first eluent; (e) contacting the first eluent (which can optionally be diluted) with a second copolymeric cation exchange column, the second copolymeric cation exchange column comprising a resin; (f) washing the second copolymeric cation exchange column after step (e) to obtain a washed second copolymeric cation exchange column; and (g) eluting the $^{68}$Ga from the washed second copolymeric cation exchange column to obtain a second eluent comprising purified $^{68}$Ga. In an embodiment, the step of washing the first chelating cation exchange column comprises contacting a first acid solution with the first chelating cation exchange column. In another embodiment, the first acid solution is a 0.01N HCl solution. In yet a further embodiment, the step of eluting the $^{68}$Ga from the washed first chelating cation exchange column comprises contacting a second acid solution with the washed first chelating cation exchange column. In yet a further embodiment, the second acid solution has a normality above that of the first acid solution. In an embodiment, the second acid solution is a 0.75N HCl solution. In yet a further embodiment, the process further comprises the step of diluting the first eluent with a third acid solution prior to contacting the first eluent with the second copolymeric cation exchange column. In yet a further embodiment, the third acid solution has a normality substantially similar that of the first solution. In yet a further embodiment, the third acid solution is a 0.01N HCl solution. In yet a further embodiment, the step of washing the second copolymeric cation exchange column comprises contacting a fourth acid solution with the second copolymeric cation exchange column. In yet a further embodiment, the fourth acid solution has a normality substantially similar to that of the first acid solution or that of the third acid solution. In yet a further embodiment, the fourth acid solution is a 0.01N HCl solution. In yet a further embodiment, the step of eluting the $^{68}$Ga from the washed second copolymeric cation exchange column comprises contacting a fifth acid solution comprising a salt with the second copolymeric cation exchange column. In yet a further embodiment, the fifth acid solution comprises a salt has a normality above that of the first acid solution. In an embodiment, the fifth acid solution is a 5.5N HCl. In yet a further embodiment, the fifth acid solution is a 5 M NaCl solution. In yet a further embodiment, the copolymeric resin comprises a silica backbone connected to two functional groups. In yet a further embodiment, the functional groups are a $C_8$ group and a benzenesulfonic acid. In an embodiment, the resin is a CUBCX123 resin. In yet a further embodiment, the process further comprises the step of irradiating a target comprising Zn with an accelerated particle beam prior to step (a). In yet a further embodiment, the accelerated particle beam is produced in a cyclotron. In yet a further embodiment, the target comprising Zn is a liquid target and the irradiated liquid target is the solution comprising a mixture of $^{68}$Zn and $^{68}$Ga. In yet a further embodiment, the target comprising $^{68}$Zn is a solid target. In yet a further embodiment, the process further comprises the step of dissolving the irradiated solid target in a dissolving acid to form the solution comprising a mixture of $^{68}$Zn and $^{68}$Ga. In yet a further embodiment, the step of dissolving the irradiated solid target comprises contacting the irradiated solid target with a sixth acid solution. In yet a further embodiment, the sixth acid solution has a normality above that of the first acid solution or the third acid solution. In yet a further embodiment, the sixth acid solution is a 7N HNO$_3$ solution. In yet a further embodiment, the sixth acid solution has a pH of at least 1.5. In yet a further embodiment, the process further comprises a step of adjusting a pH of the solution comprising a mixture of $^{68}$Zn and $^{68}$Ga prior to step (b). In yet a further embodiment, the pH is adjusted to between 1 and 3. In an embodiment, the pH is adjusted to about 2. In an embodiment, wherein the pH is adjusted with a seventh acid solution. In yet a further embodiment, the sixth acid solution is a 2.5M NH$_4$HCO$_2$ solution. In yet a further embodiment, the process has an overall recovery yield of $^{68}$Ga in the second eluent of at least 80%. In yet a further embodiment, the second eluant has an effective molar activity of $^{68}$Ga is at least 20 GBq/µmol.

According to a second aspect, the present disclosure provides a system for purifying $^{68}$Ga, the system comprising a first column comprising a hydroxamate resin; a second column comprising a copolymeric strong cation exchange resin; and a controller for purifying $^{68}$Ga according the process of the first aspect. In an embodiment, the cation exchange resin comprises a silica backbone connected to two functional groups. In another embodiment, the functional groups are a C8 group and a benzenesulfonic acid. In yet a further embodiment, the cation exchange resin is a CUBCX123 resin.

According to a third aspect, the present disclosure provides a composition obtained by the process of the first aspect or using the system of the second aspect. In an embodiment, the composition has less than 2% $^{67}$Ga and $^{66}$Ga. In another embodiment, the composition has less than 10 ppm of metallic impurities and less than 20 ppm of heavy metals. In yet a further embodiment, the composition further comprises a carrier molecule, wherein the carrier molecule is radiolabeled with the $^{68}$Ga. In yet a further embodiment, the carrier molecule is a peptide, a peptoid or a peptidomimetic. In yet a further embodiment, the peptide, peptoid or peptidomimetic is a radiopharmaceutical for positron emission tomography (PET) imaging. In yet a further embodiment, the peptide is 1,4,7,10-tetraazacyclododecane-1,4,7, 10-tetraacetic acid—Tyr(3)-Tyr(8)-octreotide (DOTA-TATE). In yet a further embodiment, a radiolabeling efficiency of DOTA-TATE with $^{68}$Ga is at least 92%. In yet a further embodiment, the carrier molecule targets a human tissue. In yet a further embodiment, the human tissue is selected from the group consisting of: thyroid, brain, gastrointestinal, pancreas, spleen, kidney, neuroendocrine tumors, renal cell carcinoma, small cell lung cancer, breast cancer, prostate cancer, and malignant lymphoma.

According to a fourth aspect, the present disclosure provides a use of the composition of the third aspect for positron emission tomography (PET) imaging.

According to a fifth aspect, the present disclosure provides a method of performing positron emission tomography (PET) imaging in a subject in need thereof, comprising administering an imaging amount of the composition of the third aspect to the subject prior to submitting the subject to PET.

BRIEF DESCRIPTION OF THE DRAWINGS

Having thus generally described the nature of the invention, reference will now be made to the accompanying drawings in which.

DETAILED DESCRIPTION $^{68}$Ga is widely used as a radioisotope in nuclear medicine and can be obtained by recovering $^{68}$Ga from cyclotron bombardment of a target of $^{68}$Zn. While $^{68}$Ga was recovered using various ion-exchange chromatography strategies, there remain a need to improve its recovery.

The present disclosure provides a process for producing and/or purifying $^{68}$Ga from an irradiated target. The process may notably be used to separate $^{68}$Ga from other radionuclides obtained by irradiating $^{68}$Zn as well as from other contaminants (e.g., metal impurities). The process relies on the use of specific resins, especially a combination of two cation exchange resins, and specific reagents that improve the yield of $^{68}$Ga recovery from the irradiated target within a timeframe compatible with the short half-life of $^{68}$Ga.

Production of Irradiation Products of $^{68}$Zn

Figure 1:
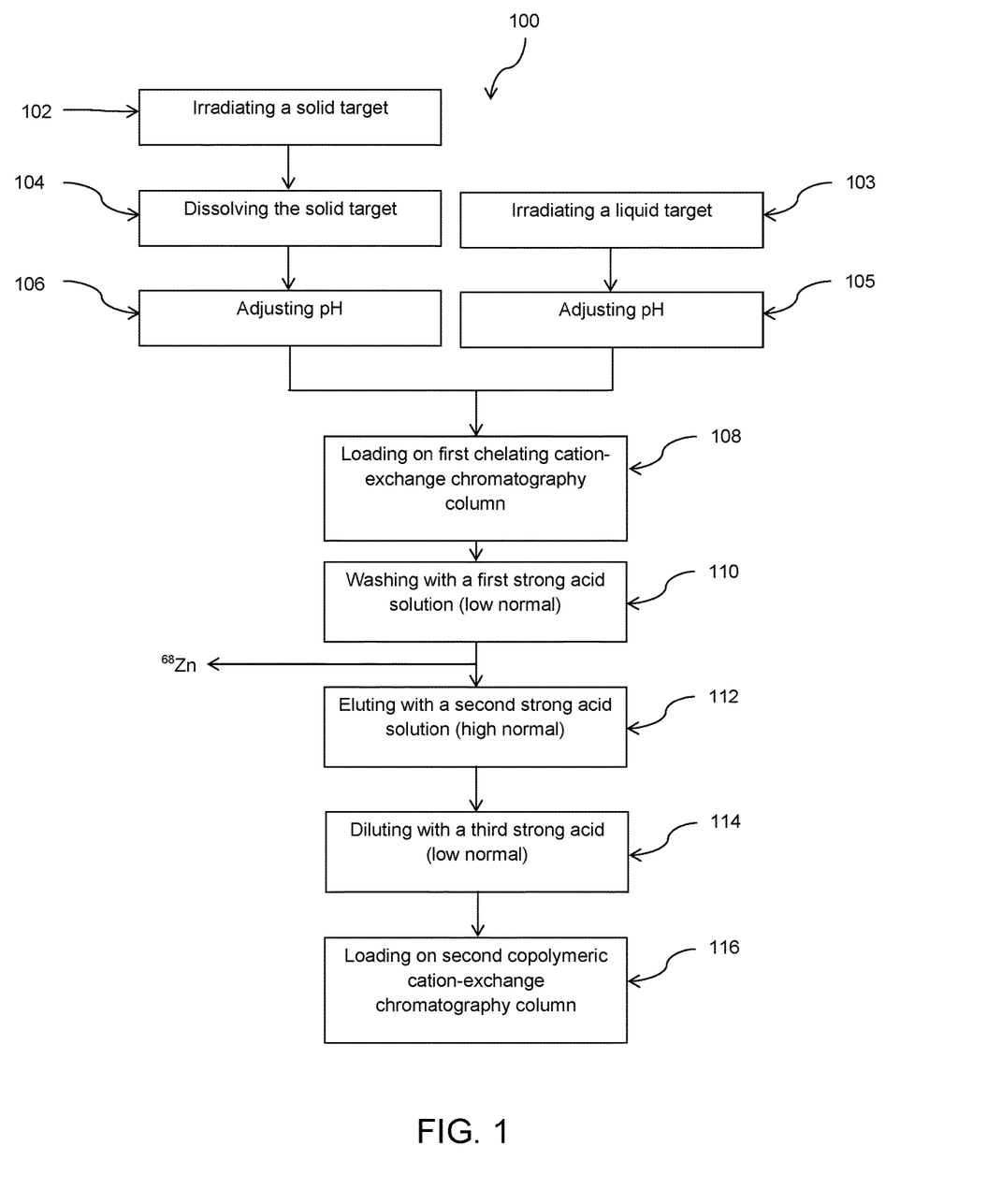
FIG. 1 shows an embodiment of a process for producing and/or purifying $^{68}$Ga from an irradiated substrate of $^{68}$Zn.

A flow chart of a process 100 that can be used to produce and/or purify $^{68}$Ga according to one non-limiting embodiment is shown in FIG. 1. A target comprising $^{68}$Zn is first irradiated by an accelerated proton beam. The target may be in liquid form or in solid form. When in solid form, the solid target comprising $^{68}$Zn may be pressed in a suitable support and then be irradiated by the proton beam (to form a solid irradiated target) at step 102 according to methods known to a person of ordinary skill in the art. The amount (mass) of $^{68}$Zn that may be irradiated may be between 50 mg and 2500 mg, preferably between 100 mg and 250 mg. When in liquid form, the liquid target (i.e., a solution) comprising $^{68}$Zn may be directly irradiated by the particle beam (to form an irradiated liquid target) at step 103 according to methods known to a person of ordinary skill in the art. The liquid target may notably comprise a $^{68}$Zn salt. A suitable Zn salt is Zn(NO$_3$)$_2$ however any other suitable salt may be used in other embodiments. Any suitable volume of liquid target may be irradiated. In one embodiment, the volume of liquid target being irradiated may be comprised between 1 mL and 7 mL, preferably between 1.5 mL and 2 mL. As a result of the irradiation, $^{68}$Ga as well other radionuclides (e.g., $^{66}$Ga, $^{67}$Ga, $^{67}$Zn and $^{66}$Zn) are produced, as further discussed below.

In this embodiment, the accelerated particle beam is a proton beam and the proton beam is produced by a cyclotron. The cyclotron may be any suitable cyclotron, such as but not limited to a low- or mid-energy cyclotron producing a proton beam in the range of 12 to 15 MeV.

At a step 104, which is specific to the solid target, the solid irradiated target (which notably comprises $^{68}$Zn, $^{68}$Ga and other radionuclides) is dissolved in an appropriate solvent (in solution) capable of dissolving the irradiated target. In one embodiment, the solvent may be a trace metals basis acid solution (i.e., the acid solution comprises no more than 0.1% (wt.) trace metals). In a preferred embodiment, the solvent may be an acid solution comprising a strong acid. The term "strong acid" as used herein means an acid with a pKa less than about −2 that ionizes completely in an aqueous solution. Examples of strong acid include but are not limited to HCl and HNO$_3$. When HCl is used, a solution of at least 5N, at least 6N, at least 7N, at least 8N, at least 9N, at least 10N, at least 11N or 12N may be used to dissolve the irradiated solid target. When HNO$_3$ is used, a solution of at least 1N, at least 2N, at least 3N, at least 4N, at least 5N, at least 6N, at least 7N, at least 8N, at least 9N or even more may be used to dissolve the irradiated solid target. In one embodiment, the irradiated solid target is added directly in a vial containing the solution of solvent for dissolution, as further described below. The volume of solvent used for the dissolution may be any volume suitable to dissolve the irradiated solid target and may need to be adapted depending on the amount of irradiated target to be dissolved, as will be appreciated by the person of ordinary skill in the art. In a preferred embodiment, the volume of solvent used for the dissolution is between 0.5 and 2.5 mL. In some embodiments, the volume of solvent used for the dissolution is about 1 mL.

It is appreciated that the time until all the irradiated solid target, or substantially all the irradiated solid target, is dissolved should be compatible with the short half-life of $^{68}$Ga. In one embodiment, dissolution of all or substantially all of the irradiated solid target is achieved in no more than 5 minutes, no more than 4 minutes, no more than 3 minutes, no more than 2 minutes, no more than 1 minute or even less.

Still in this embodiment, once the irradiated solid target has been dissolved in an appropriate solvent at step 104, the pH of the resulting solution of irradiation products of $^{68}$Zn is adjusted at a step 106 to between 1 and 3, preferably to between 1.5 and 2.5, and more preferably to about 2. Any suitable basic solution may be used to adjust the pH to the desired value. In a non-limiting embodiment, the solution may be an ammonium cation (as a base) which can be added directly in the form of a salt or as ammonia. When provided in the form of a salt, the base may be, but is not limited to: NH$_4$OH, NH$_4$HCO$_2$, NH$_4$F, NH$_4$CH$_3$CO$_2$, (NH$_4$)$_2$SO$_4$, (NH$_4$)$_2$SiO$_3$, (NH$_4$)$_3$PO$_4$, NH$_4$H$_2$PO$_4$, C$_4$H$_{12}$N$_2$O$_4$, C$_4$H$_{12}$N$_2$O$_6$, C$_6$H$_{17}$N$_3$O$_7$, (NH$_4$)$_2$CrO$_4$, (NH$_4$)$_6$Mo$_7$O$_{24}$, (NH$_4$)$_{10}$H$_2$(W$_2$O$_7$)$_6$, NH$_4$VO$_3$ or NH$_4$SCN. In this embodiment, the basic solution used to adjust the pH may have a concentration of at least 1 N, at least 1.5 N, at least 2.0 N, at least 2.5 N and even more. In a preferred embodiment, an ammonium salt which, once dissolved, evaporates easily to facilitate further downstream processing steps, is used. It is appreciated that the step adjusting the pH to the aforementioned values is not specific to the solid target and that the pH of the irradiated liquid target may also be adjusted in a similar manner at step 105 after the irradiation step 103, as shown in FIG. 1.

Process for Separating $^{68}$Ga from Other Irradiation Products and Impurities

Still with reference to FIG. 1, following the pH adjustment step 105 or 106, a solution of irradiation products of $^{68}$Zn is provided. The solution notably comprises $^{68}$Zn and $^{68}$Ga (and optionally other radionuclides and metal impurities). The solution of irradiation products of $^{68}$Zn is then loaded onto a first chelating cation-exchange chromatography column at step 108. Specifically, the solution of irradiation products of $^{68}$Zn is contacted with a polymer (usually in the form of a resin). Without wishing to be bound by any theory, $^{68}$Ga, as well as $^{68}$Zn, are adsorbed by the polymer, however their respective degree of adsorption (i.e., the strength of the ionic interaction between $^{68}$Ga, $^{68}$Zn and the column) is different. By carefully selecting washing and eluting solutions, as further discussed below, $^{68}$Zn may be eluted from the chromatography first without substantially eluting $^{68}$Ga. This therefore enables the separation, and ultimately, the recovery, of $^{68}$Ga from $^{68}$Zn. Said differently, step 108 is conducted under conditions that favor the association of $^{68}$Ga with the polymer, by contrast with $^{68}$Zn.

Hydroxamate can be used as a resin for the first chelating cation-exchange chromatography column at step 108. The resin can also be a composite of silica or low cross-linked polystyrene and 3000-4000 MW polyethylene glycol (PEG). Any suitable amount of hydroxamate may be used in the column. In a preferred embodiment, the amount of hydroxamate in the first chelating cation-exchange chromatography column may be between 200 and 350 mg, preferably the amount of hydroxamate in the column is adjusted depending upon the amount of $^{68}$Zn used (100-250 mg). In one non-limiting example, about 200 mg hydroxamate is used for about 100 mg of $^{68}$Zn. In one embodiment, the hydroxamate resin comprises hydroxamate groups bonded to a backbone comprising a material selected from the group consisting of silica, polymer-coated silica, polyacrylate, polystyrene and PEG-coated polystyrene. In another embodiment, the hydroxamate resin comprises hydroxamate groups bonded to a backbone comprising an acrylic acid/acrylamide coated silica or PEG-coated polystyrene having a narrow size distribution and excellent swelling properties. The hydroxamate resin may have a particle size in the range of 10 μm to 200 μm, preferably in the range of 50 μm to 150 μm. In some embodiments, the hydroxamate resin has a particle size 50 μm. above Any other suitable hydroxamate resin may be used in other embodiments.

It is appreciated that the first chelating cation-exchange chromatography column may also be preconditioned before step 108 according to methods and protocols known to the person of ordinary skill in the art.

After loading on the first chelating cation-exchange chromatography column at step 108, the column is then washed with a first strong trace metals basis acid solution at step 110. The washing step 110 notably removes unbound or poorly absorbed contaminants such as irradiation products ($^{68}$Zn) that may be loosely associated with the polymer. The first strong acid solution may comprise any suitable strong acid, such as but not limited to HCl or HNO$_3$. In a preferred embodiment, the first strong acid solution is a HCl solution and the first strong acid solution has a low normality, that is N may be less than 0.01 and in some cases even less. In this embodiment, the wash step 110 may accordingly be performed with large volumes of solution (when compared to the volume of the solution of irradiation products of $^{68}$Zn), for example up to 40 mL, up to 50 mL, up to 60 mL and in some cases even more. Without wishing to be bound by any theory, step 110 eliminates all or substantially all Zn (i.e., $^{68}$Zn and other isotopes) which was bound onto the first chelating cation-exchange chromatography column at step 108 which is then eluted in a container. All or substantially all $^{68}$Ga remains bound onto the first chelating cation-exchange chromatography column (as well as other radionuclides such as $^{66}$Ga and $^{67}$Ga), as further discussed below. At the end of step 110, a solution containing $^{68}$Zn is therefore obtained, which can be recycled or discarded.

$^{68}$Ga is then eluted from the column at a step 112 with a second strong acid solution. The second strong acid solution may comprise any suitable trace metals basis strong acid, such as but not limited to HCl. In a preferred embodiment, the second strong acid solution is a HCl solution and the second strong acid solution has a low normality, that is N may be at least 0.55, at least 0.65, at least 0.75, at least 0.85 and in some cases even more. In this embodiment, the elution step 112 may accordingly be performed with smaller volumes of solution (when compared to the volume of the solution of irradiation products of $^{68}$Zn), for example with less than 3 mL, less than 2 mL and in some cases even less. Without wishing to be bound by any theory, step 112 elutes all or substantially all $^{68}$Ga which was bound onto the first chelating cation-exchange chromatography column at step 108 (as well as other radionuclides such as $^{67}$Ga and $^{66}$Ga). At the end of step 112, a $^{68}$Ga-enriched eluent substantially free of $^{68}$Zn is therefore obtained.

In this embodiment, an amount of $^{68}$Ga retained onto the first chelating cation exchange chromatography column after the eluting step 112, measured in radioactivity and in % of the total radioactivity of $^{68}$Ga present in the solution of irradiation products of $^{68}$Zn (obtained after step 105/106), is less than 10%, less than 9%, less than 8%, less than 7%, less than 6% and even less. That is, the efficacy of transfer of $^{68}$Ga from the first chelating cation exchange chromatography column after the eluting step 112, measured in radioactivity and in % of the total radioactivity of $^{68}$Ga present in the solution of irradiation products of $^{68}$Zn (obtained after step 105/106), is at least at least 90%, at least 91%, at least 92%, at least 93%, at least 94% and even more.

As it is known in the art, radioactivity measurements may optionally be performed in an ionization chamber as well as by γ-ray spectrometry according to methods known to the person of ordinary skill.

At step 114, the $^{68}$Ga eluted from the first chelating cation-exchange chromatography column at step 112 is dissolved in a third trace metals basis strong acid solution to form a diluted eluent of $^{68}$Ga. In this embodiment, the third strong acid solution may be identical to the first strong acid solution or substantially similar to the first strong acid solution, (that is, the third strong acid solution may have a normality that is within ±5% of the normality of the first strong acid solution). The third trace metals basis strong acid solution may comprise any suitable strong acid, such as but not limited to HCl and preferably the third strong acid solution is a HCl solution with a low normality, that is N may be less than 0.01 and in some cases even less. The use of HCl may be advantageous in instances in which it is desired to obtain GaCl$_3$. The third strong acid solution may be any other suitable solution in other embodiments. In this embodiment, the $^{68}$Ga eluted from the first chelating cation-exchange chromatography column may be diluted at step 114 with a dilution factor of 1:4 or any other suitable dilution factor in other embodiments.

The diluted eluent from step 114 is then loaded onto a second copolymeric cation-exchange chromatography column at step 116. In this embodiment, the second copolymeric cation-exchange chromatography column of step 116 is different from the first chelating cation-exchange chromatography column of step 108. Specifically, the eluent is contacted with another polymer in the form of a resin which is different from the polymer of the first chelating cation-exchange chromatography column of step 108. The resin can also be cross-linked with two types of functional chains. Any suitable amount of resin may be used in the column. In one non-limiting embodiment, the amount of resin in the second copolymeric cation-exchange chromatography column may be between 100 and 300 mg, preferably the amount of resin in the column is about 200 mg. The resin of the second copolymeric cation-exchange chromatography column may comprise a silica backbone bonded with two types of functional chains attached—an anion exchanger or polar chain and a hydrophobic carbon chain. Preferably, the functional anion exchanger group may be a benzenesulfonic acid and the hydrophobic chain may be an octyl chain (C$_8$)—such resin is available commercially as the CUBCX123 column. Any other suitable (commercially-available) column or functional group may be used in other embodiments.

It is appreciated that the second copolymeric cation-exchange chromatography column may also be preconditioned according to protocols known to the person of ordinary skill in the art.

After loading on the second copolymeric cation-exchange chromatography column at step 116, the column is then washed with a fourth strong acid solution at step 118. The washing step 118 removes and, in some embodiment, depletes or substantially depletes metal and cation contaminants which may be present in the diluted eluent of $^{68}$Ga at step 114. In this embodiment, the fourth trace metals basis strong acid solution may be identical to the first strong acid solution or substantially similar to the first trace metals basis strong acid solution, (that is, the fourth trace metals basis strong acid solution may have a normality that is within ±5% of the normality of the first strong acid solution). The fourth trace metals basis strong acid solution may comprise any suitable strong acid, such as but not limited to HCl, HNO$_3$, HBr, HClO$_3$, HClO$_4$ and H$_2$SO$_4$, preferably the fourth strong acid solution is a HCl solution with a low normality, that is N may be less than 0.01 and in some cases even less. The wash step 118 may therefore be performed with large volumes of solution (when compared to the volume of eluted and diluted $^{68}$Ga at step 114), for example at least 20 mL, at least 30 mL, at least 40 mL and in some cases even more.

$^{68}$Ga is then eluted from the second copolymeric cation-exchange chromatography column at a step 120 with a salt/trace metals basis strong acid solution. The salt/trace metals basis strong acid solution may comprise any suitable strong acid, such as but not limited to HCl. In a preferred embodiment, the salt/strong acid solution comprises HCl with a high normality, that is N may be at least 5, at least 5.5 and in some cases even more. The salt/strong acid solution also comprises a salt, such as but not limited to NaCl. The salt may be present at a concentration of at least 5 M and even more. In this embodiment, the elution step 120 may be performed with larger volumes of solution (when compared to the volume of the eluted and diluted $^{68}$Ga solution obtained at the end of step 114), for example with more than 10 μL, more than 15 μL, more than 20 μL, more than 25 μL and in some cases even more. Without wishing to be bound by any theory, step 120 elutes all or substantially all $^{68}$Ga which was bound onto the second copolymeric cation-exchange chromatography column at step 116 (as well as other radionuclides such as $^{66}$Ga and $^{67}$Ga). It is appreciated that notably because of the presence of NaCl in the salt/trace metals basis strong strong acid solution, $^{68}$Ga is eluted at step 120 in the form of [$^{68}$Ga] GaCl$_3$. At the end of step 120, a $^{68}$Ga-enriched eluent substantially free of $^{68}$Zn and other metal impurities is therefore obtained.

In this embodiment, an amount of $^{68}$Ga retained onto the second copolymeric cation exchange chromatography column after the eluting step 120, measured in radioactivity and in % of the total radioactivity of $^{68}$Ga present in the solution of irradiation products of $^{68}$Zn (obtained after step 105/106), is less than 0.55%, less than 0.4%, less than 0.3%, less than 0.2%, less than 0.1% and even less. That is, the overall recovery yield of the purification process, that is the radioactivity fraction of $^{68}$Ga eluted at step 120 in the form of [$^{68}$Ga] GaCl$_3$ compared to the total radioactivity of $^{68}$Ga present in the solution of irradiation products of $^{68}$Zn (obtained after step 105/106) is at least 80%, at least 82%, at least 84%, at least 85%, at least 86%, at least 87%, at least 88% or more. Still in this embodiment, the EMA of [$^{68}$Ga] GaCl$_3$ isolated according to the process 100 for a solid or a liquid target is at least 24 GBq/µmol, at least 25 GBq/µmol and in some cases even more.

Radionuclide impurities (including $^{67}$Ga and $^{66}$Ga) in the $^{68}$Ga-enriched eluent obtained at the end of step 120 may be present at a concentration of less than 2% $^{67}$Ga at 6 h post irradiation while a concentration of $^{66}$Ga is negligible at 6 h post irradiation (i.e., 6 hours post-completion of step 102/103). It is appreciated that the presence of such radionuclide impurities should be measured by taking into account the longer half-life of $^{67}$Ga ($T_{1/2}$=3.26d) and $^{66}$Ga ($T_{1/2}$=9.45 h).

Still in this embodiment, metal impurities (including heavy metals) in the $^{68}$Ga-enriched eluent obtained at the end of step 120 may be present at a concentration less than 10 ppm and in some cases even less. Similarly, in this embodiment, impurities including aluminum, iron, magnesium, molybdenum, zinc, copper may be present at a concentration of less than 5 ppm, less than 4 ppm, less than 3 ppm, less than 2 ppm and even less in the $^{68}$Ga-enriched eluent obtained at the end of step 120. Antimony, barium, beryllium, bismuth, cadmium, chromium, cobalt, lead, lithium, molybdenum, selenium, silver, titanium and vanadium may be present at a concentration of less than 0.05 ppm, less than 0.04 ppm, less than 0.03 ppm, less than 0.02 ppm and even less in the $^{68}$Ga-enriched eluent obtained at the end of step 120. Measurements of the concentration of metallic impurities may be performed by inductively-coupled plasma mass spectrometry (ICP-MS) according to methods and protocols known to the person of ordinary skill in the art.

It is appreciated that the process 100, or any subset of the process 100, may be automated. That is, and with further reference to FIG. 2, in one non-limiting embodiment a system 200 for the automated purification of $^{68}$Ga may be implemented. While it is appreciated that system 200 as shown is designed for solid targets, any other system suitable for liquid targets may be provided in other embodiments. Also, while system 200 is only concerned with the purification of $^{68}$Ga (and therefore does not cover steps 102/103 of the process 100 for the irradiation of the target), the system 200 may also automate both the separation of $^{68}$Ga (from the target of $^{68}$Zn) and the purification of $^{68}$Ga in other embodiments such that the irradiation (and transfer) of the target at step 102 may also be automated in the context of the system 200. As further described below, the system 200 of FIG. 2 is configured to automate the steps 104, 105/106, 108, 110, 112, 114, 116, 118 and 120 of the process 100.

Figure 2:
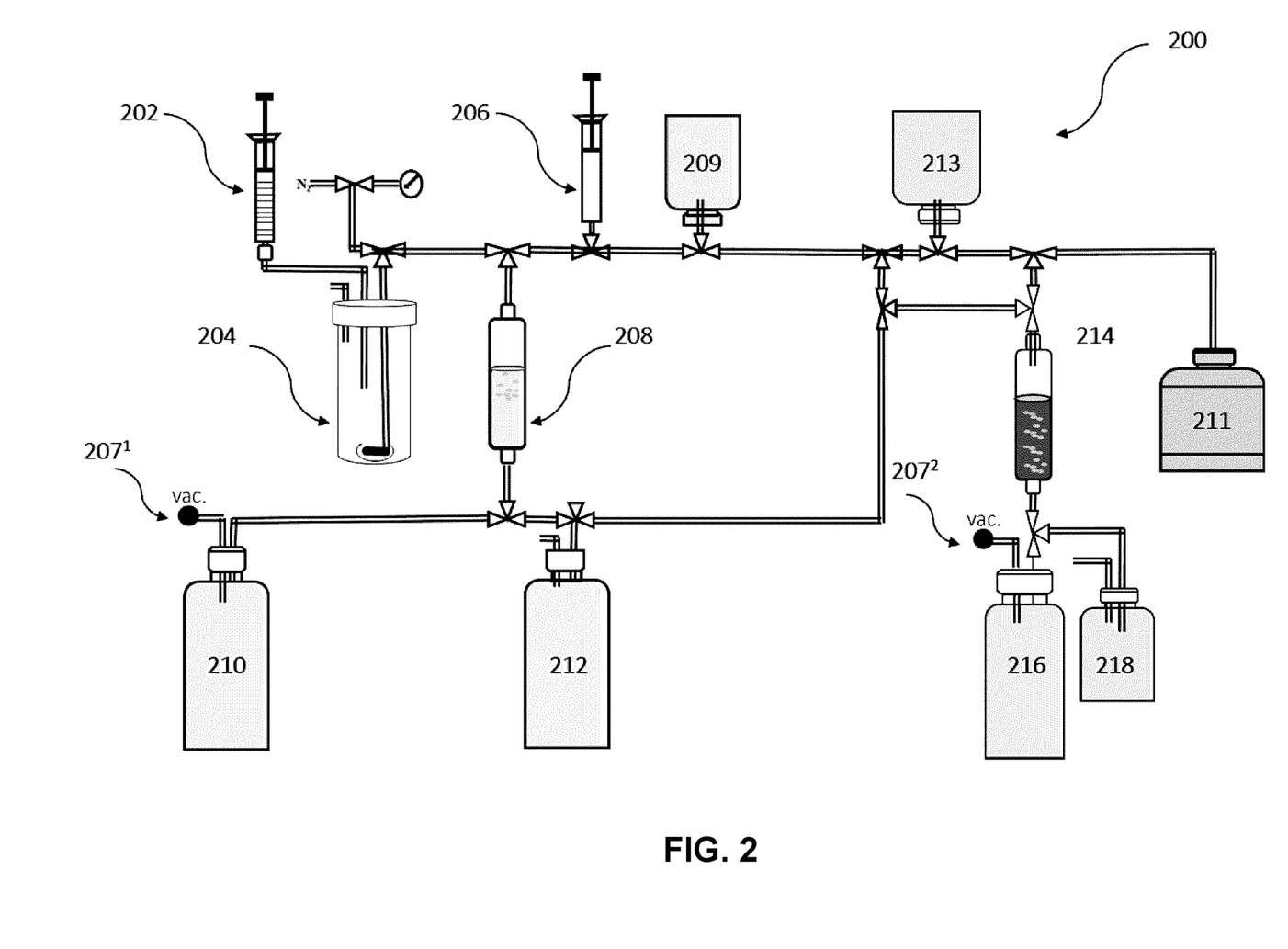
FIG. 2 shows an embodiment of an automated system for purifying $^{68}$Ga using the process of FIG. 1.

In one non-limiting embodiment, and with further reference to FIG. 2, the step 104 of dissolving the solid irradiated target is performed in a vial 204 containing the solvent required for the dissolution and in which the solid irradiated target is added. The step 106 of adjusting the pH is performed via a syringe 202 containing a solution (basic or acid). The step 108 of loading onto the first chelating cation-exchange chromatography column 208 is achieved by creating a negative pressure in the system 200 via a vacuum pump connected to a first valve 207$^1$. Once loaded, the step 110 of washing the first chelating cation-exchange chromatography column 208 and the step 112 of eluting the first chelating cation-exchange chromatography column 208 are achieved via a syringe 206 in which the relevant first and second trace metals basis strong acid solutions are added. This can notably be achieved through the vial 211 containing a low normal trace metals basis HCl solution and eluting through the vial 209 containing a low normal HCl solution, the solutions being loaded in the syringe 206 and passed through the first chelating cation-exchange chromatography column 208 using the negative pressure created by the vacuum pump connected to the first valve 207$^1$. The solution containing $^{68}$Zn obtained at the end of step 110 is collected in a vial 210 while the $^{68}$Ga-enriched eluent substantially free of $^{68}$Zn obtained at the end of step 112 is collected in a vial 212 in which the step 114 of dilution through a vial 211 with the third low normal trace metals basis strong acid solution is also performed via the syringe 206. At step 116, the diluted $^{68}$Ga-enriched eluent is then loaded onto the second copolymeric cation-exchange chromatography column 214, again by creating a negative pressure in the system 200 via the vacuum pump connected to a second valve 207$^2$. Once loaded, the step 118 of washing the second copolymeric cation-exchange chromatography column 214 and the step 120 of eluting the second copolymeric cation-exchange chromatography column 214 are achieved via the syringe 206 in which the relevant fourth strong acid solution and salt/strong acid solution are added. This can notably be achieved washing through the vial 211 containing the low normal HCl solution and eluting through the vial 213 containing the salt/trace metals basis strong acid solution, the solutions being loaded in the syringe 206 and passed through the second copolymeric cation-exchange chromatography column 214 using the negative pressure created by the vacuum pump connected to the second valve 207$^2$. The solution obtained at the end of step 118 is collected in a vial 216 while the $^{68}$Ga-enriched eluent substantially free of $^{68}$Zn obtained at the end of step 120 is collected in a product vial 218. It is appreciated that these various elements are all interconnected in the context of a computer-based cassette-based module via liquid and gas connections as well as switches, as shown in FIG. 2. Any other suitable configuration is possible in other embodiments in order to achieve the process shown in FIG. 1.

In this embodiment, the system 200 is operated by the cassette-based module which is controlled by a software (not shown) such that the various syringes 202, 206, vacuum pumps 207$^1$, 207$^2$, liquid and gas connections and switches may all be operated entirely automatically via the software to perform the various steps of the process 100. In this embodiment, the process 100 implemented by the system 200 may be entirely performed in less than 15 min and in some cases even less.

In one non-limiting embodiment, $^{68}$Ga produced according to the process 100 may be attached to a carrier molecule to form a radioactive tracer, which finds applications notably in PET scans. $^{68}$GaCl$_3$ produced by cyclotron is also useful as a radiopharmaceutical when attached to a pharmaceutical moiety.

Generally, $^{68}$GaCl$_3$ produced by cyclotron and purified according to the process 100 may be attached to the carrier molecule by incubating the carrier molecule, at a pre-determined concentration, in a solution comprising the purified $^{68}$GaCl$_3$, the solution being at a pre-determined pH (i.e., between 2 and 4 in a non-limiting embodiment), the incubation being at a high temperature (i.e., above 80° C. in a non-limiting embodiment), as further described below.

The term carrier molecule as used herein means a drug, protein, antibody, antibody fragment, peptide, peptide fragment, amino acid or particle, which when introduced into the body by injection, swallowing, or inhalation accumulates in one or more organs or tissues of interest. The organ(s) or tissue(s) where accumulation occurs is said to be the target organ(s) or target tissue(s) of the carrier molecule, Examples of carrier molecules include but are not limited to: 1,4,7,10-tetraazacyclododecane-1,4,7,10-tetraacetic acid (DOTA); diethylene triamine pentaacetic acid (DTPA); 1,4,7-triazacyclononane-1,4,7-triacetic acid (NOTA); 2-hydroxy-11,16,20-tris(4-(hydroxy(methyl)amino)-4-oxobutanoyl)-3,6-dioxo-2,7,11,16,20-pentaazadocosan-22-oic acid (4HSMA), Desferrioxamine (Dfo), DOTA-PSMA, DOTA-Tyr(3)-octreotide (DOTATOC), DOTA-Tyr(3)-Tyr(8)-octreotide (DOTATATE); DOTA-1-naphtyl-alanine (DOTANOC); DOTA-benzothienyl-alanine (DOTA-BOC); DOTA-bombesin; DOTA-arginine-glycine-aspartic acid-bombesin (DOTA-RGD-bombesin); 1,4,7-triazacyclononane-1,4,7-triacetic acid-RGD (NOTA-RGD); 3,6,9,15-tetraazabicyclo[9.3.1]pentadeca-1(15), 11,13-triene-3,6,9-triacetic acid-RGD (PCTA-RGD); DOTA-albumin; DOTA-human epidermal growth factor; 1,4,7-triazacyclononane-1-methyl[(2-carboxyethyl) phospinic acid]-4,7-bis[methyl(2-hydroxymethyl) phosphinic acid-integrin alpha(IIb)beta(3)-specific cyclic hexapeptide (NOPO-RGDfK); 1,4,7-triazacyclononane-1,4-bis(acetic acid)-7-(2-glutaric acid) (NODAGA); NOPO-Nal(3)-octreotide conjugate (NOPO-NOC); and 1,4,7-triazacyclononane-1,4,7-tris[(2-carboxyethyl) methylenephosphinic acid] (TRAP(RGD)3); 4HSMA-PSMA; 4HSMA-TOC; 4HSMA-TATE; 4HSMA-NOC; 4HSMA-benzothienyl-alanine; 4HSMA-bombesin; 4HSMA-RGD (monomer, dimer, trimer and tetramer); 4HSMA-albumin; 4HSMA-human epidermal growth factor. Examples of targets include but are not limited to: thyroid, brain, gastrointestinal, pancreas, spleen, kidney, neuroendocrine tumors, renal cell carcinoma, small cell lung cancer, breast cancer, prostate cancer, and malignant lymphoma.

In one non-limiting embodiment, for attaching $^{68}$Ga purified via the method 100 to a carrier such as DOTA-TATE, DOTA-TATE peptide may be dissolved in high purity water containing $^{68}$Ga. Specifically, the pH of the solution of $^{68}$Ga-enriched eluent substantially free of $^{68}$Zn and other metal impurities obtained the end of step 122 may be adjusted to a pH of between 2.5 and 3.5, preferably between 3.0 and 3.2 using a solution of acid. Any suitable acid may be used. In this embodiment, the acid is preferably NH$_4$OAc at a concentration of 1M. DOTA-TATE at a concentration of 20 nmol may be dissolved in high-purity water containing $^{68}$Ga purified via the method 100 and the resulting solution may be incubated at a temperature of 100° C. for 12 min in presence of ascorbic acid, ethanol or gentisic acid. In this embodiment, the radiolabelling efficiency of the $^{68}$Ga-DOTA-TATE peptide is at least 92%, at least 93%, at least 94%, at least 95%, at least 96% and even more.

The composition of the present disclosure can be used to perform positron emission tomography (PET) in a subject in need thereof. In such embodiment, the composition can be diluted with a carrier suitable for performing PET. The composition can be provided in an imaging amount to the subject so as to allow performance of the PET.

The present disclosure will be more readily understood by referring to the following examples which are given to illustrate the invention rather than to limit its scope.

EXAMPLE

Chemicals and equipment. All chemicals and solvents were purchased with high purity and used directly unless otherwise specified. Enriched $^{68}$Zn powder (99.26%) was purchased from ISOFLEX USA (San Francisco, CA). Trace metals basis hydrochloric acid (HCl 99.999%), 70% nitric acid (HNO$_3$, ≥99.999%), ammonium carbonate (Na$_2$CO$_3$, 99.999%), ammonium formate (NH$_4$HCO$_2$, ≥99.995%) and $^{nat}$Zn (99.995%) were purchased from Sigma-Aldrich (Saint-Louis, MO, USA). High-purity water (Optima LC/MS, ultra-high performance liquid chromatography ultraviolet grade, 0.03 mm filtered), acetonitrile (HPLC grade, 99.9%), methanol (HPLC grade, ≥99.9%) and sodium chloride (NaCl) were purchased from Fisher Scientific (Ottawa, ON, CA). Hydroxamate resin was prepared following the procedure reported by Verel et al. (2003) and was packed in a 1 mL cartridge between two frits (20 microns, United chemical technologies, Bristol, PA, USA). Propylsulfonic resin (CUBCX123, 200 mg) was bought from UCT, Inc (Bristol, PA, USA). IGG100 $^{68}$Ge/$^{68}$Ga Generator was obtained from Eckert and Ziegler EUROTOPE GmbH (Berlin, Germany). Instant thin-layer chromatography-silica gel (ITLC-SG) and glass microfiber chromatography paper impregnated with silica gel was obtained from Agilent Technologies (Santa Clara, CA, USA).

All glass vials were cleaned with chromic-sulfuric acid solution obtained from Fisher Scientific and rinsed with high-purity water. The labeling efficiency of $^{68}$Ga-DOTA-TATE was determined using radio-ITLC-SG with 1M NH$_4$OAc:MeOH (50:50,v:v) as the mobile phase. The radio-ITLC plates were scanned using an instant imager scanner (Canberra Packard, Austria). Radioactivity measurements were performed in an ionization chamber (CRC-25PET; Capintec) on the $^{68}$Ga setting to control process efficiency and by γ-ray spectrometry with a calibrated high-purity germanium detector (GMX HPGe; ORTEC) for analytic quantitation. Experimental samples were counted for 5-10 min on a using a dynamic energy windows of 1-2000 keV. All radiation detection devices were calibrated and maintained in accordance with known control procedures.

Optimization of $^{68}$Ga purification process on hydroxamate resin. $^{68}$Ga purification conditions were optimized using natural Zn ($^{nat}$Zn) pressed target and generator-produced [$^{68}$Ga]GaCl$_3$. In this non-limiting example, the target is a solid/pressed target of $^{68}$Zn/$^{68}$Ga and two cation exchange resins are used for purification including a hydroxamate resin for the first step (Verel et al., 2003) and CUBCX123 resin for the second step of the purification (Mueller et al., 2012), as further described below.

A MiniAlO cassette-based module from Trasis (Ans, Belgium) was used for the automated purification of $^{68}$GaCl$_3$, in accordance with the system 200 of FIG. 2. Prior to perform purification, the two 6-positions cassettes and the solution vials were installed and the unit was cleaned using 7N $HNO_3$ and 0.01N HCl. To reduce exposure to metals that can affect EMA, all liquid and gas connections were assembled using polytetrafluoroethylene (PTFE) tubing and silicon connectors. A solution of base (1N $NH_4OH$ or 2.5N $NH_4HCO_2$) was inserted in the syringe 202 that was directly connected to the dissolution vial 204 to adjust pH after dissolution. Eluents used for the washing and rinsing steps (in the vials 209, 211 and 213) were transferred via the syringe 206. To avoid solvent leaks, the other solutions were transferred through the system using a negative pressure (800 mbar) generated by the vacuum pump connected to the valves $207^1$ and $207^2$. The first chelating cation-exchange chromatography column 208 comprising the hydroxamate resin was preconditioned with 10 mL of acetonitrile, 20 mL of high-purity water, 2 mL of 2N HCl and finally rinsed with 20 mL water or more instead a pH at least of 4 is reached. The second copolymeric cation-exchange chromatography column 214 comprising the CUBCX123 resin (200 mg) was preconditioned with 2 mL 6N HCl and 5 mL of high-purity water. The purification process was controlled by a laptop computer running Trasis-MiniAlO Software-Version 2.0 Rev 22.

Target dissolution. Solutions of HCl and $HNO_3$ at different concentrations were tested for target dissolution at room temperature using 100-250 mg of $^{nat}Zn$ solid (pressed) target. The total volume used for the dissolution was set at 1 mL. A magnetic stirring bar was installed in the dissolution vial 204 during the dissolution and pH adjustment to homogenize the solution. $^{68}Ga$ has a short half-life and a fast target dissolution in a low volume of solvent is mandatory. Two different acids were used for this purpose and the results are shown in Table 1. For the dissolution, 100 mg of $^{nat}Zn$-pressed target was dissolved in 1 mL solution for entries 1 to 6, 165 mg of $^{nat}Zn$-pressed target was dissolved in 1 mL solution for entry 7 and 250 mg of $^{nat}Zn$-pressed target was dissolved in 1 mL solution for entry 8.

TABLE 1

Dissolution times of $^{nat}Zn$ solid targets

| Entry | Acid concentration[a] | Volume (mL) | Time (min) |
|---|---|---|---|
| 1 | HCl (8N) | 1 | >20 |
| 2 | HCl (10N) | 1 | 8 |
| 3 | HCl (12N) | 1 | 1.5 |
| 4 | $HNO_3$ (4N) | 1 | >15 |
| 5 | $HNO_3$ (6N) | 1 | 1.6 |
| 6 | $HNO_3$ (7N) | 1 | 1 |
| 7 | $HNO_3$ (7N)[b] | 1.5 | 1 |
| 8 | $HNO_3$ (7N)[c] | 2 | 1 |

[a]100 mg of $^{nat}Zn$-pressed target was dissolved in 1 mL solution;
[b]165 mg of $^{nat}Zn$-pressed target;
[c]250 mg of $^{nat}Zn$-pressed target.

The fastest times of dissolution for the ~100 mg $^{nat}Zn$-pressed target were 1.5 min and 1 min using 12N HCl and 7N $HNO_3$ respectively (Table 1, entries 3 and 6). The volumes of 7N $HNO_3$ were increased to 1.5 and 2 mL to dissolve completely in ~1 min the 165 and 250 mg $^{nat}Zn$-pressed targets respectively (Table 1, entries 7-8).

pH adjustment for $^{68}Ga$ transfer and elution on hydroxamate resin. After $^{nat}Zn$ target dissolution (95-250 mg), generator-produced $^{68}Ga$ (in 0.1N HCl, 4.5 mL) was added to the dissolution vial 204. The solution of base (1N $NH_4OH$ or $NH_4HCO_2$) in the syringe 202 was added in the dissolution vial 204 to adjust the pH between 0.5-3.5 before transferring the resulting crude solution to the first chelating cation-exchange chromatography column 208 comprising the hydroxamate resin (the resin comprising between 100 and 250 mg of hydroxamate). The resulting crude solution was then loaded on and passed through to the hydroxamate resin and recuperated in the vial 210 using a negative pressure created by the vacuum pump $207^1$. Because of the ion exchange occurring on the hydroxamate resin, all or substantially all of the $^{68}Ga$ remained on the first chelating cation-exchange chromatography column 208 at this stage, as further discussed below, while the vial 210 contains a solution free or substantially free of $^{68}Ga$. An additional 5×10 mL of high-purity water or 0.01N HCl (pH 2) was the eluted on the first chelating cation-exchange chromatography column 208 and recuperated in the vial 210. Solutions of HCl at different concentrations (0.5-2 N) were then tested for elution of $^{68}Ga$ in the vial 212. After each modification, $^{68}Ga$-activity was measured by a dose calibrator in the dissolution vial 204, the first chelating cation-exchange chromatography column 208 and the vials 210 and 212.

Optimization of the $^{68}Ga$ purification process for cyclotron produced [$^{68}Ga$]$GaCl_3$. In one non-limiting example, the $^{68}Zn/^{68}Ga$ pressed target (95-250 mg) was dropped in the dissolution vial 204, which contained 1-2 mL of 7M $HNO_3$. A solution of $NH_4HCO_2$ (2-2.5 mL, 2.5M) was then added to the dissolution vial 204 to adjust the pH to about 2. The resulting crude solution was then loaded and passed through the first chelating cation-exchange chromatography column 208 comprising the hydroxamate resin (200-330 mg) and into the vial 210 using a negative pressure created by the vacuum pump connected to the first valve $207^1$. The first chelating cation-exchange chromatography column 208 was then washed with 0.01N HCl (50 mL) to remove $^{68}Zn$. $^{68}Ga$ was then eluted from the first chelating cation-exchange chromatography column 208 with 0.75N HCl (2 mL) to the vial 212 as [$^{68}Ga$]$GaCl_3$. The solution in the vial 212 was diluted using 0.01 N HCl (8 mL) and loaded onto the second copolymeric cation-exchange chromatography column 214 comprising the CUBCX123 resin. The second copolymeric cation-exchange chromatography column 214 was washed with 0.01N HCl (30 mL) into the vial 216. Finally, [$^{68}Ga$]$GaCl_3$ was eluted from the second copolymeric cation-exchange chromatography column 214 to the product vial 218 using NaCl 5M (500 μL)/HCl 5.5N (12.5 μL) from the vial 213 (Mueller et al., 2012).

Different pH values were tested to evaluate the efficacy of transfer of $^{68}Ga$ from dissolved target solution in the dissolution vial 204 onto the chelating first chelating cation-exchange chromatography column 208 comprising the hydroxamate resin. The process was followed by recording the percentage of $^{68}Ga$ activity remaining in the dissolution vial 204 and on the first chelating cation-exchange chromatography column 208. The results are summarized in Table 2. The pH was adjusted using $NH_4OH$ (1 M) after dissolving $^{nat}Zn$ (60 mg) in 1 mL $HNO_3$ (7 N).

TABLE 2

Efficacy of transfer of $^{68}Ga$ from the dissolution vial to the first chelating cation-exchange chromatography column at different pH values

| Entry | pH | $^{68}Ga$ activity in dissolution vial 204 (%) | $^{68}Ga$ activity in retained on the resin 208 (%) |
|---|---|---|---|
| 1 | 0.5 | 0.4 | 5.7 |
| 2 | 1 | 0.2 ± 0.0 | 47.6 ± 1.3 |
| 3 | 1.5 | 0.2 ± 0.0 | 89.2 ± 1.6 |
| 4 | 2 | 0.4 ± 0.4 | 97.0 ± 2.1 |

TABLE 2-continued

Efficacy of transfer of $^{68}$Ga from the dissolution vial to the first chelating cation-exchange chromatography column at different pH values

| Entry | pH | $^{68}$Ga activity in dissolution vial 204 (%) | $^{68}$Ga activity in retained on the resin 208 (%) |
|---|---|---|---|
| 5 | 3 | 2.9 ± 1.6 | 99.7 ± 0.1 |
| 6 | 3.5 | 11.7 ± 1.0 | 99.4 ± 0.3 |

The $^{68}$Ga activity was efficiently transferred from the dissolution vial 204 to the first chelating cation-exchange chromatography column 208 for pH between 0.5-3 (Table 2, entries 1-5). However, at low pH (0.5-1.5), $^{68}$Ga was not efficiently retained on the first chelating cation-exchange chromatography column 208 (Table 2, entries 1-3). At pH greater than 3, $^{68}$Ga remained in the dissolution vial 204 (Table 2, entries 5-6). A longer time is required for transferring the dissolved target solution from the dissolution vial 204 at pH 3.5.

High-purity water (40 mL) was first used for rinsing the first chelating cation-exchange chromatography column 208 of residual traces of $^{68}$Zn and other metal impurities to the vial 210. Using this eluent, the pH increased from 2 to 7 with the risk to form insoluble metal species. 0.01N HCl (40 mL) was used as a rinsing solution for maintaining the pH at 2 during this step. The pH should preferably be maintained between 2 and 3 in order to minimize $^{68}$Ga activity in the dissolution vial 204 and retain $^{68}$Ga on the first chelating cation-exchange chromatography column 208 (Table 2, entries 4-5).

Different HCl concentrations were compared for eluting $^{68}$Ga from the first chelating cation-exchange chromatography column 208 and results are shown in Table 3. Initially, 100 mg of hydroxamate resin 208 was used in combination with a 2 mL HCl solution to minimize elution time.

TABLE 3

Percentage of $^{68}$Ga-activity eluted from hydroxamate resin using different HCl concentrations

| Entry | [HCl] (N)$^a$ | $^{68}$Ga activity eluted in vial 212 (%) |
|---|---|---|
| 1 | 0.5 | 80.6 ± 3.5 |
| 2 | 0.75 | 88.65 ± 1.3 |
| 3 | 1 | 97.7 ± 1.3 |
| 4 | 2 | 99.9 ± 0.1 |

$^a$100 mg of resin was used for a 2 mL HCl solution.

At 0.5N and 0.75N HCl, 80% and 89% of the $^{68}$Ga activity were respectively transferred to the vial 212 (Table 3, entries 1-2). The highest transfer yields were found with 1N and 2N HCl solutions (Table 3, entries 3-4).

Figure 3:
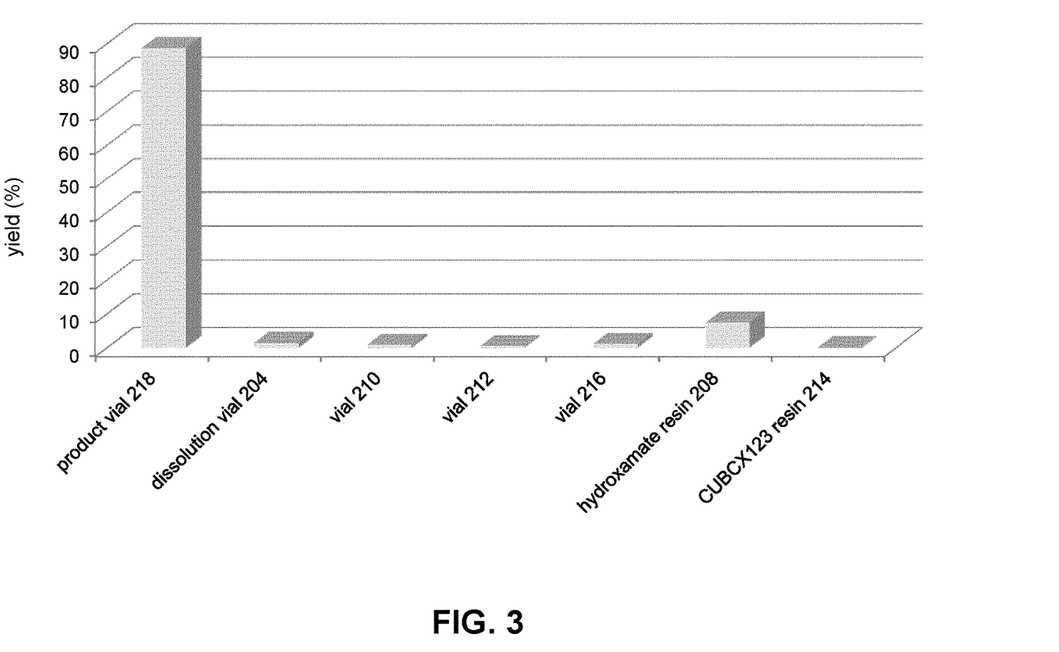
FIG. 3 shows a yield of recovery (in %) of $^{68}$Ga as well as losses of $^{68}$Ga (in %) in the various components of the system of FIG. 2.

Determination of the overall recovery yield. With further reference to FIG. 3, the overall recovery yield was 88.7±1.4% with minimal losses found mainly in the hydroxamate resin (7.4±0.1%), dissolution vial (1.4±1.1%), vial 1 (0.9±0.2%) and vial 3 (1.1±0.6%). In this non-limiting example, the complete procedure takes approximately 10 min from target dissolution to formulation of [$^{68}$Ga]GaCl$_3$.

Determination of radionuclide and metal impurities. Samples containing 148-222 kBq of purified $^{68}$GaCl$_3$ in a 1.5 mL microcentrifuge tube were diluted with high-purity water to bring a final volume of 0.5 mL. The radionuclidic purity was determined by γ-ray spectroscopy on a high purity germanium (HPGe) detector with a zoom energy window of 1-2000 KeV. Using this amount of radioactivity, the dead time was below 5 second. Samples were counted for only 5-10 minutes after end of synthesis. In addition, the tests were repeated after two days to qualify radionuclide impurities with long half-life such as $^{67}$Ga ($T_{1/2}$=3.26 d). The half-life was estimated using dose calibrator CRC-55 PET. Trace metal analysis in [$^{68}$Ga]GaCl$_3$ solution was performed by inductively coupled plasma mass spectroscopy (ICP-MS) for 26 elements in compliance with USP <233> (Exova, St-Augustin-de-Desmaures, Canada).

Figure 4A:
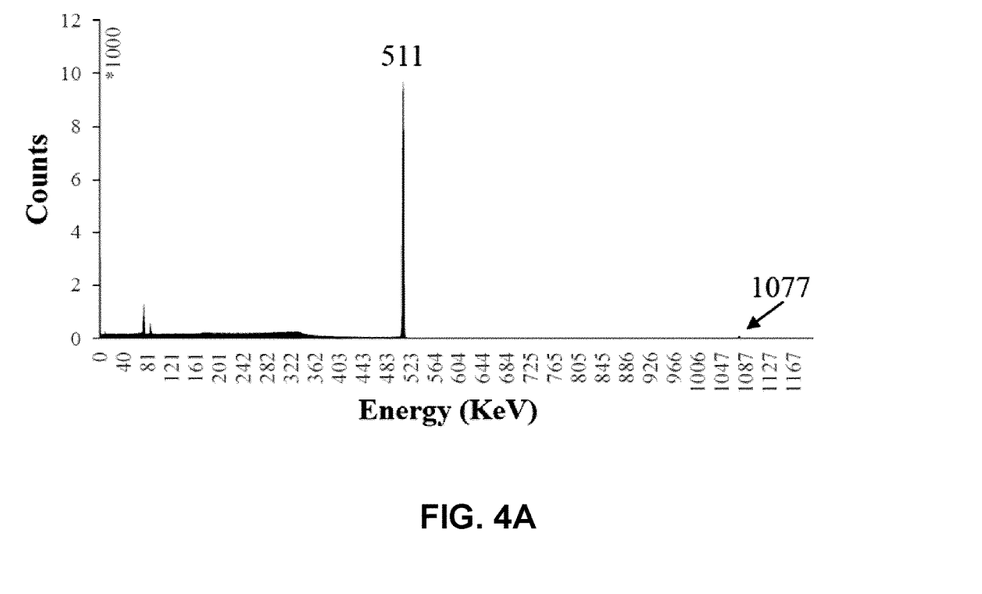
FIG. 4A shows a representative γ-spectra of $^{68}$Ga and $^{66/67}$Ga after completed purification in the system of FIG. 2.
Figure 4B:
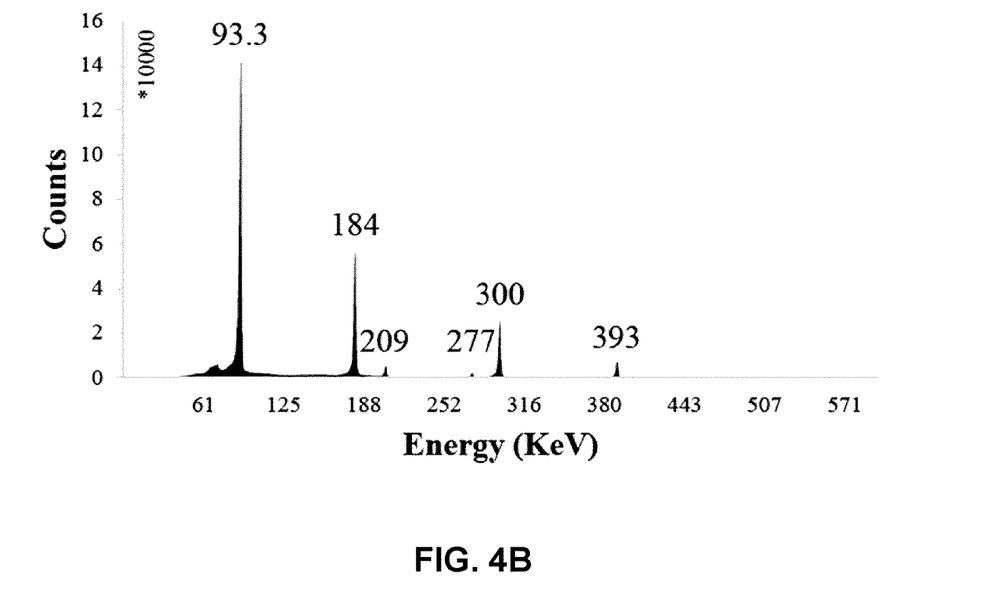
FIG. 4B shows a representative γ-spectra of $^{68}$Ga and $^{66/67}$Ga 72 hours after completed purification in the system of FIG. 2.

With further reference to FIGS. 4A and 4B, two peaks with high intensity at 511 and 1079 KeV were observed after purification corresponding to $^{68}$Ga. In addition, measurements were repeated 72 h post purification and three peaks corresponding to the $^{67}$Ga impurity were clearly observed on the γ-ray spectrum. The main radionuclide impurities observed were $^{67}$Ga ($T_{1/2}$=3.26d) and $^{66}$Ga ($T_{1/2}$=9.45 h), but amount was limited <0.01% at EOB or <2% after 7 h post irradiation. Specifically, the amount of impurities were as follows: $^{67}$Ga: 0.0106±0.0039% and $^{66}$Ga: 0.0093±0.0045% at EOB with an excitation of 13 MeV.

Metal impurities in purified [$^{68}$Ga]—GaCl$_3$ solution were identified by ICP-MS and compared to generator-produced with the results shown in Table 4.

TABLE 4

Trace metal analysis by ICP-MS.

| [$^{68}$Ga]-GaCl$_3$ | Metal (ppm) | | | | | | | |
|---|---|---|---|---|---|---|---|---|
| | Al | Ca | Fe | Mg | Mo | Zn | Cu | K |
| Cyclotron (2 mL)$^a$ | <2.5 | 8.34 | <12.5 | <2.5 | <2.5 | 7.56 | <2.5 | <75 |
| Cyclotron (0.5 mL)$^b$ | <1.12 ± 0.87 | 2.67 ± 0.47 | <3.34 ± 1.18 | <0.67 ± 0.23 | <0.07 ± 0.02 | 2.21 ± 0.32 | <0.07 ± 0.02 | <20 ± 7.07 |
| Generator (0.7 mL)$^c$ | 2.5 ± 1.15 | 20.45 ± 0.35 | <2.5 ± 0.0 | 1.21 ± 0.01 | <0.05 ± 0.0 | 1.07 ± 0.44 | <0.06 ± 0.01 | <15 ± 0.0 |

$^a$After first purification using hydroxamate resin (n = 1).
$^b$Final product (n = 2).
$^c$Final product (n = 2).

For all tested batches, metallic impurities were below the general limit of 10 ppm and 20 ppm for heavy metals in the U.S. and Europe. Impurity concentrations of aluminum, iron, magnesium, molybdenum, zinc, copper were <5 ppm and antimony, barium, beryllium, bismuth, cadmium, chromium, cobalt, lead, lithium, molybdenum, selenium, silver, tin, titanium, vanadium were <0.02 ppm.

Calculation of effective molar activity. EMA (GBq/μmol) of $^{68}$Ga was calculated via titration with DOTA and the purified [$^{68}$Ga]GaCl$_3$. Solutions of DOTA (145 μL in 4 mL polypropylene tube) at different concentrations (1.8 to 3.5× $10^{-3}$ nmol) were prepared via serial dilution. [$^{68}$Ga]GaCl$_3$ solution was adjusted to a final pH of 3.0-3.2 with NH$_4$OAc buffer (1M pH=4.5) and added (10-20 μL, ~3.7 MBq) to each tube to give a total volume of 160-170 μL. After mixing (vortex) and 12 min incubation at 100° C., the EMA was determined by measuring DOTA labeling efficiency in each tube by TLC using 1N NH$_4$OAc:MeOH (50:50, v:v) as mobile phase. When using ITLC-SG, [$^{68}$Ga]GaCl$_3$ remains at the origin, and complexed [$^{68}$Ga]Ga-DOTA migrates with the solvent front. TLC plates were analyzed using a radio-TLC scanner. The percentages of complexation were plotted in function of amount of chelator (nmol) and the EMA was determined when >95% complexation was realized.

With further reference to FIG. 4, the EMA of [$^{68}$Ga]—GaCl$_3$ for solid (pressed) target was 25±0.18 GBq/μmol. This value was comparable to that obtained for [$^{68}$Ga]—GaCl$_3$ produced by generator of 34±0.18 GBq/μmol.

Radiolabeling of $^{68}$Ga-DOTA-TATE. DOTA-TATE peptide was labeled with cyclotron-produced [$^{68}$Ga]GaCl$_3$ following conditions optimized in our laboratory. Briefly, DOTA-TATE (21 nmol) was dissolved in high purity water (1 mL) with [$^{68}$Ga]GaCl$_3$ (~555 MBq, pH 3.1, 250 μL); the resulting solution was incubated 12 min at 100° C. The pH of [$^{68}$Ga]GaCl$_3$ (500 μL) was adjusted to pH 3.0-3.2 using 1M NH$_4$OAc (pH 4.5). After the incubation time, the labeling efficiency was determined by iTLC using 1M NH$_4$OAc:MeOH (50:50, v:v) as a mobile phase. When using ITLC-SG, [$^{68}$Ga]GaCl$_3$ remains at the origin, and complexed [$^{68}$Ga]Ga-DOTA-TATE migrates with the solvent front. The labeling efficiency was also determined by radio-UPLC (Waters Acquity) using an ACQUITY UPLC® BEH C18 1.7 μm column (2.1 μm×50 mm, Waters acquity) with a gradient of 0-100% acetonitrile (0.4% AcOH) in high purity water over 7.5 min.

Figure 5:
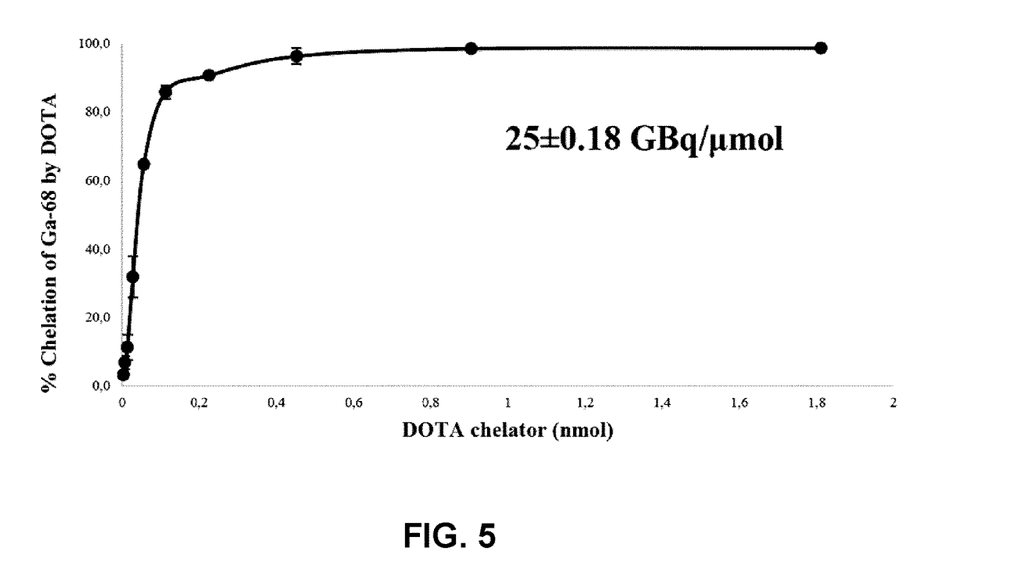
FIG. 5 shows an EMA curve of purified [$^{68}$Ga]GaCl$_3$ using 1,4,7,10-tetraazacyclododecane-1,4,7,10-tetraacetic acid (DOTA) ligand titration, using the process of FIG. 1A and the system of FIG. 2, in accordance with one embodiment.
Figure 6:
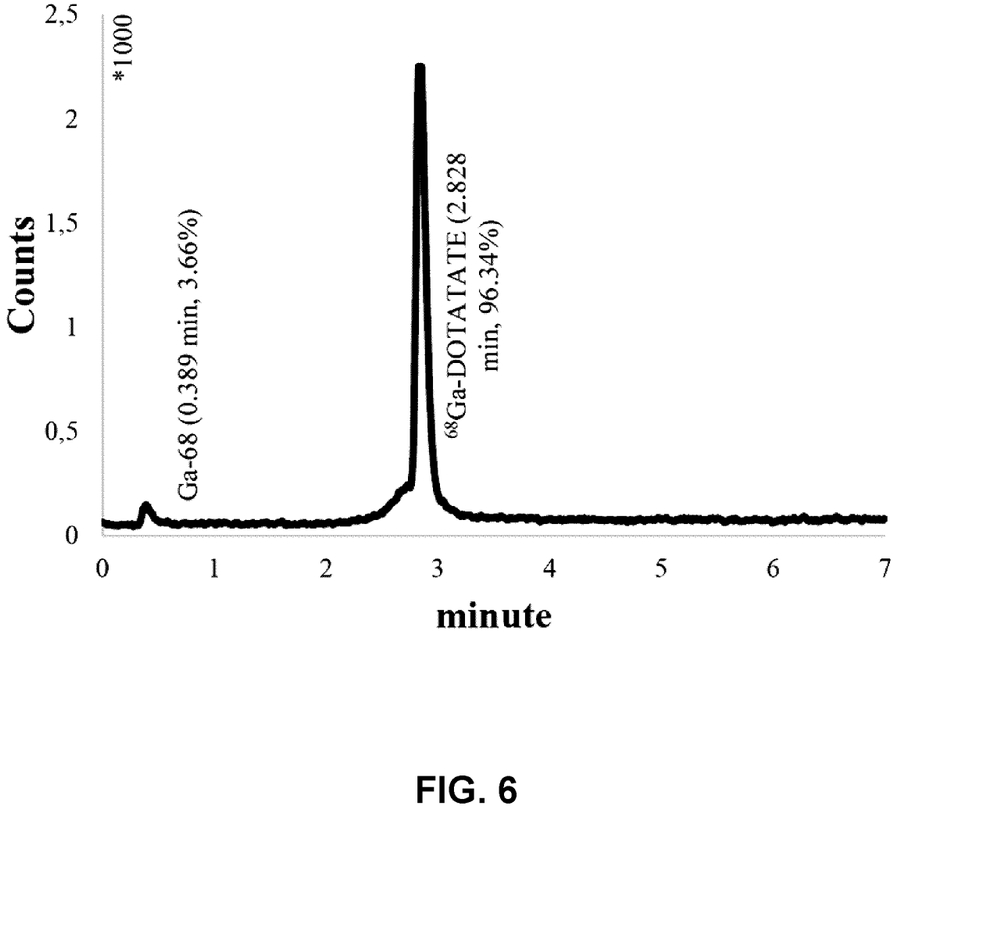
FIG. 6 shows an ultra-performance liquid chromatography (UPLC) chromatogram for $^{68}$Ga-DOTA-Tyr(3)-Tyr(8)-octreotide ($^{68}$Ga-DOTA-TATE) peptide in accordance with one embodiment.

With further reference to FIG. 5, The radiolabelling efficiency for $^{68}$Ga-DOTA-TATE peptide was 95±1.6% by UPLC.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Alves, F., Alves, V. H., Neves, A. C. B., Do Carmo, S. J. C., Nactergal, B., Hellas, V., Kral, E., Gonçalves-Gameiro, C., Abrunhosa, A. J., 2017. Cyclotron production of Ga-68 for human use from liquid targets: From theory to practice. AIP Conf. Proc. 1845. https://doi.org/10.1063/1.4983532

Blaser, J. P., Boehm, F., Marmier, P., Peaslee, D. C., 1950. Fonctions d'excitation de la réaction (p,n). (I). Helv. Phys. Acta 24, 3-38.

Hermanne, A., 1997. Evaluated cross section and thick target yield data of Zn+P processes for practical applications Private communication. Exfor: D4093 49

Howe, H. A., 1958. (p,n) Cross Sections of Copper and Zinc. Phys. Rev. 109, 6-8

Lin, M., Waligorski, G. J., Lepera, C. G., 2018. Production of curie quantities of 68Ga with a medical cyclotron via the 68Zn(p,n)68Ga reaction. Appl. Radiat. Isot. 133, 1-3. https://doi.org/10.1016/j.apradiso.2017.12.010

Mueller, D., Klette, I., Baum, R. P., Gottschaldt, M., Schultz, M. K., Breeman, W. A. P., 2012. Simplified NaCl based68Ga concentration and labeling procedure for rapid synthesis of 68Ga radiopharmaceuticals in high radiochemical purity. Bioconjug. Chem. 23, 1712-1717. https://doi.org/10.1021/bc300103t Nortier, F. M., Stevenson, N. R., Gelbart, W. Z., 1995. Investigation of the thermal performance of solid targets for radioisotope production. Nucl. Instruments Methods Phys. Res. Sect. A Accel. Spectrometers, Detect. Assoc. Equip. 355, 236-241. https://doi.org/10.1016/0168-9002(94)01110-9

Pandey, M. K., Byrne, J. F., Jiang, H., Packard, A. B., Degrado, T. R., 2014. Cyclotron production of 68Ga via the 68Zn(p,n)68Ga reaction in aqueous solution. Am. J. Nucl. Med. Mol. Imaging 4, 303-310.

Szelecsenyi, F., Boothe, T. e., Takács, S., Tárkányi, F., Tavano, E., 1998. Evaluated Cross Section and Thick Target Yield Data Bases of Zn+p Processes for Practical Applications. Appl. Radiat. Isot. 49, 1005-1032.

Velikyan, I., 2015. 68Ga-based radiopharmaceuticals: Production and application relationship, Molecules. https://doi.org/10.3390/molecules200712913

Verel, I., Visser, G. W. M., Boellaard, R., Marijke, Walsum, S.-V., Snow, G. B., Van Dongen, G. A. M. S., 2003. 89 Zr Immuno-PET: Comprehensive Procedures for the Production of 89 Zr-Labeled Monoclonal Antibodies. J Nucl Med 44, 1271-1281.

What is claimed is:

1. A process for purifying $^{68}$Ga produced by cyclotron, the process comprising the steps of:
    (a) providing a solution comprising a mixture of $^{68}$Zn and $^{68}$Ga;
    (b) contacting the solution with a first chelating cation exchange column, the first chelating cation exchange column comprising a hydroxamate resin;
    (c) washing the first chelating cation exchange column obtained after step (b) to obtain a washed first chelating cation exchange column;
    (d) eluting the $^{68}$Ga from the washed first chelating cation exchange column to obtain a first eluent;
    (e) contacting the first eluent with a second copolymeric cation exchange column, the second copolymeric cation exchange column comprising a resin;
    (f) washing the second copolymeric cation exchange column after step (e) to obtain a washed second copolymeric cation exchange column; and
    (g) eluting the $^{68}$Ga from the washed second copolymeric cation exchange column to obtain a second eluent comprising purified $^{68}$Ga.

2. The process according to claim 1, wherein the step of washing the first chelating cation exchange column comprises contacting a first acid solution with the first chelating cation exchange column.

3. The process according to claim 1, wherein the step of eluting the $^{68}$Ga from the washed first chelating cation exchange column comprises contacting a second acid solution with the washed first chelating cation exchange column.

4. The process according to claim 3, wherein the second acid solution has a normality above that of the first acid solution.

5. The process according to claim 1, further comprising the step of diluting the first eluent with a third acid solution prior to contacting the first eluent with the second copolymeric cation exchange column.

6. The process according to claim 5, wherein the third acid solution has a normality substantially similar that of the first solution.

7. The process according to claim 1, wherein the step of washing the second copolymeric cation exchange column comprises contacting a fourth acid solution with the second copolymeric cation exchange column.

8. The process according to claim 7, wherein the fourth acid solution has a normality substantially similar to that of the first acid solution or that of the third acid solution.

9. The process according to claim 1, wherein the step of eluting the $^{68}$Ga from the washed second copolymeric cation exchange column comprises contacting a fifth acid solution comprising a salt with the second copolymeric cation exchange column.

10. The process according to claim 9, wherein the fifth acid solution comprising the salt has a normality above that of the first acid solution.

11. The process according to claim 1, wherein the copolymeric resin comprises a silica backbone connected to two functional groups.

\* \* \* \* \*